United States Patent
Kodaira (10) Patent No.: US 12,278,010 B2
(45) Date of Patent: Apr. 15, 2025

(54) MEDICAL IMAGE DISPLAY APPARATUS, METHOD, AND PROGRAM

(71) Applicant: FUJIFILM CORPORATION, Tokyo (JP)

(72) Inventor: Shunsuke Kodaira, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 189 days.

(21) Appl. No.: 17/821,475

(22) Filed: Aug. 23, 2022

(65) Prior Publication Data

US 2023/0102745 A1 Mar. 30, 2023

(30) Foreign Application Priority Data

Sep. 27, 2021 (JP) .................. 2021-157097

(51) Int. Cl.
*G16H 30/40* (2018.01)
*G06T 11/60* (2006.01)
*G06F 3/04842* (2022.01)

(52) U.S. Cl.
CPC ............. *G16H 30/40* (2018.01); *G06T 11/60* (2013.01); *G06F 3/04842* (2013.01); *G06T 2200/24* (2013.01); *G06T 2210/41* (2013.01)

(58) Field of Classification Search
CPC ..... G16H 30/40; G06T 11/60; G06T 2200/24; G06T 2210/41; G06F 3/04842
See application file for complete search history.

(56) References Cited

U.S. PATENT DOCUMENTS

| 2007/0286469 A1 | 12/2007 | Yamagata et al. | |
| 2015/0149190 A1* | 5/2015 | Chace | G16H 40/20 705/2 |
| 2018/0060488 A1* | 3/2018 | Reicher | G16H 50/20 |
| 2018/0285434 A1* | 10/2018 | Shiibashi | G06F 16/27 |

(Continued)

FOREIGN PATENT DOCUMENTS

| JP | 2006-115921 A | 5/2006 |
| JP | 2008-12291 A | 1/2008 |
| JP | 2009-223595 A | 10/2009 |

OTHER PUBLICATIONS

De Carvalho Filho, Antonio Oseas, Silva, A. C., de Paiva, A. C., Nunes, R. A., & Gattass, M. (2017). Computer-aided diagnosis system for lung nodules based on computed tomography using shape analysis, a genetic algorithm, and SVM. Medical and Biological Engineering and Computing, (Year: 2017).*

(Continued)

*Primary Examiner* — Matthew L Hamilton
(74) *Attorney, Agent, or Firm* — SOLARIS Intellectual Property Group, PLLC (57) ABSTRACT

The processor displays a medical image, receives an input of a primary interpretation result by a user interpreting the medical image, displays an annotation representing the primary interpretation result, acquires an analysis result for the medical image, displays an annotation representing the analysis result, receives an input of a secondary interpretation result by the user interpreting the medical image after displaying the analysis result, and displays the annotation representing the primary interpretation result and an annotation representing the secondary interpretation result in a distinguishable manner.

9 Claims, 10 Drawing Sheets

(56) References Cited

U.S. PATENT DOCUMENTS

| | | | |
|---|---|---|---|
| 2019/0096060 A1* | 3/2019 | Zhang | G06T 7/0014 |
| 2021/0201086 A1* | 7/2021 | Wu | G06F 18/214 |
| 2021/0216822 A1* | 7/2021 | Paik | G16H 15/00 |
| 2021/0313043 A1* | 10/2021 | Kecskemethy | G06V 30/19173 |
| 2023/0260119 A1* | 8/2023 | Soeda | G06T 7/0012 |
| | | | 382/128 |

OTHER PUBLICATIONS

English language translation of the following: Office action dated Jan. 28, 2025 from the JPO in a Japanese patent application No. 2021-157097 corresponding to the instant patent application. This office action translation is submitted now in order to supplement the understanding of the cited references which are being disclosed in the instant Information Disclosure Statement.

* cited by examiner

MEDICAL IMAGE DISPLAY APPARATUS, METHOD, AND PROGRAM

CROSS REFERENCE TO RELATED APPLICATIONS

The present application claims priority under 35 U.S.C. § 119 to Japanese Patent Application No. 2021-157097, filed on Sep. 27, 2021. The above application is hereby expressly incorporated by reference, in its entirety, into the present application.

BACKGROUND

Technical Field

The present disclosure relates to a medical image display apparatus, method, and program.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, image diagnosis is made by analyzing a medical image via computer-aided diagnosis (CAD) using a learning model in which machine learning is performed by deep learning or the like, and detecting abnormal shadows such as a lesion included in the medical image from the medical image. In this way, the analysis result generated by the analysis process via CAD is saved in a database in association with examination information, such as a patient name, gender, age, and a modality which has acquired a medical image, and provided for diagnosis. A doctor interprets a medical image by referring to a distributed medical image and analysis result in his or her own interpretation terminal. At this time, a radiologist adds annotations to abnormal shadows included in the medical image based on the interpretation result. For example, a region surrounding the abnormal shadow, a mark such as an arrow indicating the abnormal shadow, text indicating the type, size, and the like of the disease, and the like are added as annotations. In addition, at the time of referring to the analysis result, an annotation representing the analysis result is displayed on the medical image.

On the other hand, the interpretation of the medical image by the doctor should not be guided by the analysis result via CAD. Therefore, the analysis result of the medical image via CAD is often used as a secondary interpretation (second reading) in the clinical field. For example, at the time of interpretation, the doctor first performs a primary interpretation of the medical image without referring to the analysis result via CAD, and adds an annotation representing the interpretation result to the medical image. After that, the medical image to which the annotation is added based on the analysis result via CAD is displayed, and the doctor performs the secondary interpretation of the medical image while referring to the annotation representing the analysis result. By performing such primary and secondary interpretations, it is possible to prevent the diseased region from being overlooked.

In addition, a method for efficiently performing interpretation by a doctor has been proposed. For example, in JP2006-115921A, a method has been proposed in which an analysis result via CAD and an interpretation result by a doctor are displayed in a superimposed manner or the analysis result and the interpretation result are displayed in parallel after a primary interpretation performed by the doctor is completed.

In some cases, the doctor wishes to correct the result of the primary interpretation after referring to the analysis result via CAD. In this case, if the result of the primary interpretation is completely deleted, or if the interpretation result is given to the medical image in the same display mode before and after the reference of the analysis result via CAD, it becomes difficult to understand how the analysis result via CAD affected the final interpretation result of the doctor.

SUMMARY OF THE INVENTION

The present disclosure has been made in view of the above circumstances, and an object thereof is to make it possible to ascertain how an analysis result of a medical image via CAD affected an interpretation result of a doctor.

According to an aspect of the present disclosure, there is provided a medical image display apparatus comprising at least one processor, in which the processor is configured to display a medical image, receive an input of a primary interpretation result by a user interpreting the medical image, display an annotation representing the primary interpretation result, acquire an analysis result for the medical image, display an annotation representing the analysis result, receive an input of a secondary interpretation result by the user interpreting the medical image after displaying the analysis result, and display the annotation representing the primary interpretation result and an annotation representing the secondary interpretation result in a distinguishable manner.

Examples of the "annotation" include a mark indicating the region surrounding the abnormal shadow pointed out by interpretation or detected by analysis and the position of the abnormal shadow, and text indicating the property, size, and the like of the abnormal shadow.

In the medical image display apparatus according to the aspect of the present disclosure, the processor may be configured to display the annotation representing the primary interpretation result and the annotation representing the secondary interpretation result in a distinguishable manner by displaying the annotation representing the primary interpretation result and the annotation representing the secondary interpretation result by means of at least one of marks having different colors or marks having different shapes.

In the medical image display apparatus according to the aspect of the present disclosure, the processor may be configured to display the annotation representing the primary interpretation result and the annotation representing the secondary interpretation result in a distinguishable manner by displaying text indicating the primary interpretation result as the annotation representing the primary interpretation result, and displaying text indicating the secondary interpretation result as the annotation representing the secondary interpretation result.

In the medical image display apparatus according to the aspect of the present disclosure, the processor may be configured to display the annotation representing the primary interpretation result and the annotation representing the analysis result in a distinguishable manner.

In the medical image display apparatus according to the aspect of the present disclosure, the processor may be configured to prohibit editing of the primary interpretation result after displaying the annotation representing the analysis result.

In the medical image display apparatus according to the aspect of the present disclosure, the processor may be configured to give a notification indicating that editing of the primary interpretation result is prohibited before displaying the annotation representing the analysis result.

In the medical image display apparatus according to the aspect of the present disclosure, the processor may be configured to display the annotation representing the primary interpretation result such that prohibition of the editing is visually recognized.

In the medical image display apparatus according to the aspect of the present disclosure, the processor may be configured to save the annotation representing the primary interpretation result and the annotation representing the secondary interpretation result in association with the medical image.

According to another aspect of the present disclosure, there is provided a medical image display method comprising: displaying a medical image; receiving an input of a primary interpretation result by a user interpreting the medical image; displaying an annotation representing the primary interpretation result; acquiring an analysis result for the medical image; and displaying an annotation representing the analysis result; receiving an input of a secondary interpretation result by the user interpreting the medical image after displaying the analysis result; and displaying the annotation representing the primary interpretation result and an annotation representing the secondary interpretation result in a distinguishable manner.

In addition, a program for causing a computer to execute the medical image display method according to the aspect of the present disclosure may be provided.

According to the aspects of the present disclosure, it is possible to ascertain how the analysis result of the medical image via CAD affected the interpretation result of the doctor.

DETAILED DESCRIPTION

Figure 1:
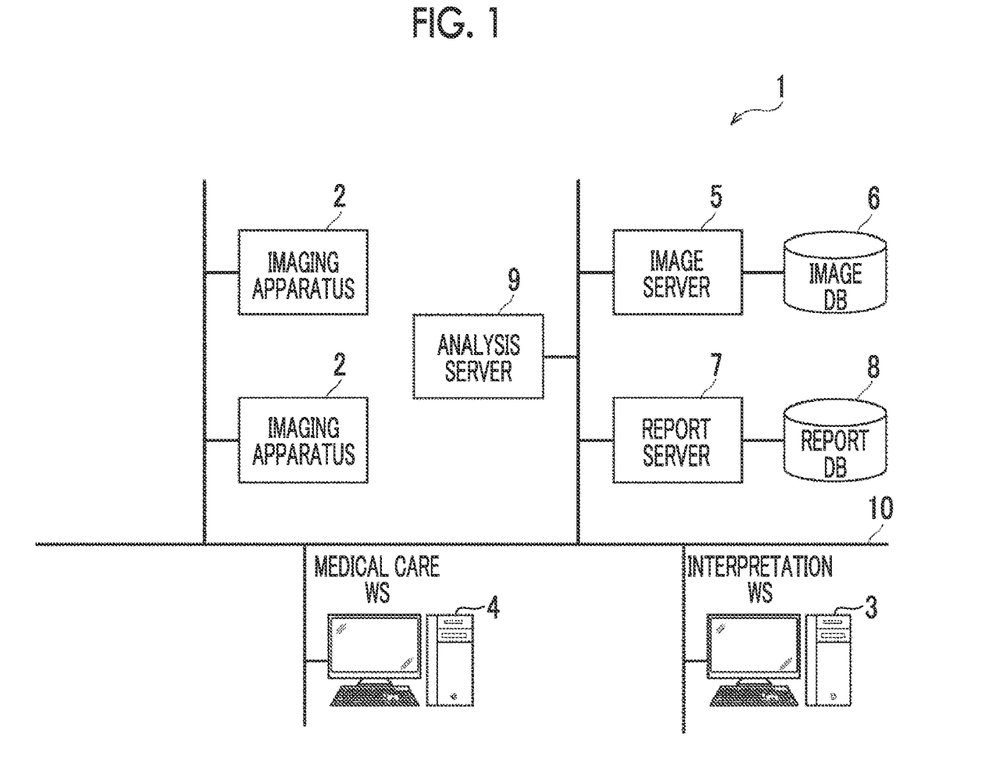
FIG. 1 is a diagram showing a schematic configuration of a medical information system to which a medical image display apparatus according to an embodiment of the present disclosure is applied.

Hereinafter, embodiments of the present disclosure will be described with reference to the drawings. First, a configuration of a medical information system 1 to which a medical image display apparatus according to the present embodiment is applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, a report database (hereinafter referred to as a report DB) 8, and an analysis server 9 are communicably connected to each other through a wired or wireless network 10.

Each apparatus is a computer on which an application program for causing each apparatus to function as a component of the medical information system 1 is installed. The application program is stored in a storage apparatus of a server computer connected to the network 10 or in a network storage in a state in which it can be accessed from the outside, and is downloaded to and installed on the computer in response to a request. Alternatively, the application program is recorded on a recording medium, such as a digital versatile disc (DVD) and a compact disc read only memory (CD-ROM), and distributed, and is installed on the computer from the recording medium.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MM apparatus, a positron emission tomography (PET) apparatus, and the like. The medical image generated by the imaging apparatus 2 is transmitted to the image server 5 and is saved in the image DB 6. The simple X-ray imaging apparatus is an apparatus that acquires a two-dimensional radiation image, which is a transmitted image of a subject, by irradiating the subject with radiation once.

The interpretation WS 3 is a computer used by, for example, a radiologist of a radiology department to interpret a medical image and to create an interpretation report, and encompasses a medical image display apparatus 20 according to the present embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, creation of an interpretation report, a registration request and a viewing request for the interpretation report to the report server 7, display of the interpretation report received from the report server 7, and the like are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report created by the radiologist using the interpretation WS 3 is registered. The interpretation report may include information such as, for example, a medical image to be interpreted, an image ID for identifying the medical image, a radiologist ID for identifying the radiologist who performed the interpretation, a disease name, disease position information, and information for accessing a medical image.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

The analysis server 9 has a software program installed on a computer that provides a function of analyzing a medical image via CAD or the like and detecting an abnormal shadow such as a lesion. A medical image analysis process on the analysis server 9 is performed according to instructions from the medical care WS 4 or the interpretation WS 3. In a case where the analysis server 9 receives instructions for the medical image analysis process, the analysis server 9 acquires the medical image to be processed from the image server 5. Then, the analysis server 9 analyzes the acquired medical image and transmits the analysis result to the medical care WS 4 or the interpretation WS 3 that has given the instructions. Further, the analysis result is transmitted to the image server 5 and is registered in the image DB 6. Examples of the analysis results include region information indicating the position of the abnormal shadow in the medical image specified by the analysis, contour information indicating the position of the contour of the abnormal shadow, coordinate information indicating the center position of the abnormal shadow, size information indicating the size of the abnormal shadow, and text information indicating the property of the abnormal shadow.

The analysis process via CAD can be performed by using a learning model in which machine learning is performed to detect an abnormal shadow from a medical image. The learning model consists of a convolutional neural network (CNN) in which deep learning has been performed using supervised training data so as to discriminate whether or not each pixel (voxel) in a medical image represents an abnormal shadow.

The learning model is constructed by training CNN using, for example, a large amount of supervised training data consisting of supervised training images that include abnormal shadows, a region of the abnormal shadows in the supervised training images, and correct answer data representing the properties of the abnormal shadows, and a large amount of supervised training data consisting of supervised training images that do not include abnormal shadows. The learning model derives the confidence degree (likelihood) indicating that each pixel in the medical image is an abnormal shadow, detects a region consisting of pixels whose confidence degree is equal to or higher than a predetermined threshold value as a region of the abnormal shadows, and derives the properties of the detected abnormal shadows. Here, the confidence degree is a value of 0 or more and 1 or less.

Further, as the learning model, any learning model such as, for example, a support vector machine (SVM) can be used in addition to the convolutional neural network.

In the present embodiment, it is assumed that the medical image is a radiation image acquired by a simple X-ray imaging apparatus whose diagnosis target is the lung, and the analysis server 9 detects the abnormal shadow included in the lung via CAD and derives the property of the abnormal shadow. The image is not limited to a radiation image, and may be a CT image or an MRI image consisting of a plurality of tomographic images.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
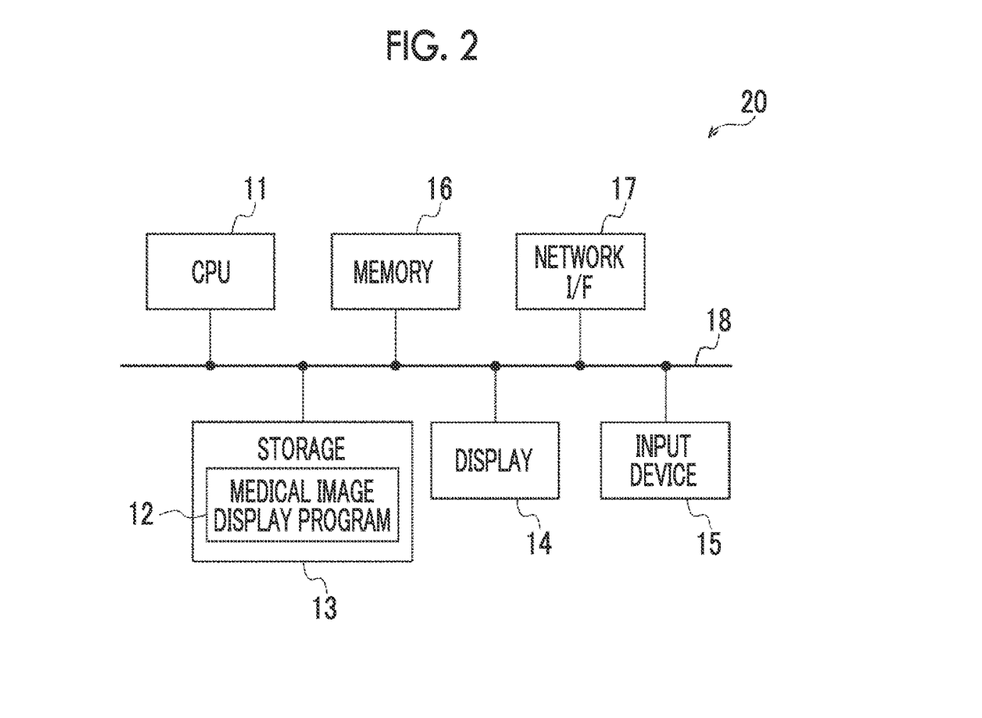
FIG. 2 is a diagram showing a schematic configuration of the medical image display apparatus according to the present embodiment.

Next, the medical image display apparatus according to the present embodiment will be described. FIG. 2 illustrates a hardware configuration of the medical image display apparatus according to the present embodiment. As shown in FIG. 2, the medical image display apparatus 20 includes a central processing unit (CPU) 11, a non-volatile storage 13, and a memory 16 as a temporary storage area. Further, the medical image display apparatus 20 includes a display 14 such as a liquid crystal display, an input device 15 consisting of a pointing device such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. A medical image display program 12 is stored in the storage 13 as the storage medium. The CPU 11 reads out the medical image display program 12 from the storage 13, loads the read-out program into the memory 16, and executes the loaded medical image display program 12.

Here, in the present embodiment, at the time of creating the interpretation report in the interpretation WS 3, the radiologist gives an analysis instruction of the medical image to the analysis server 9. Then, the radiologist displays the medical image on the display 14 and interprets the medical image with his/her own eyes. After that, the radiologist acquires the analysis result of the medical image from the analysis server 9, displays an annotation representing the analysis result on the medical image based on the acquired analysis result, and performs a second interpretation with reference to the displayed annotation representing the analysis result. The first interpretation is referred to as a primary interpretation, and the second interpretation with reference to the analysis result after the analysis result is displayed is referred to as a secondary interpretation.

Figure 3:
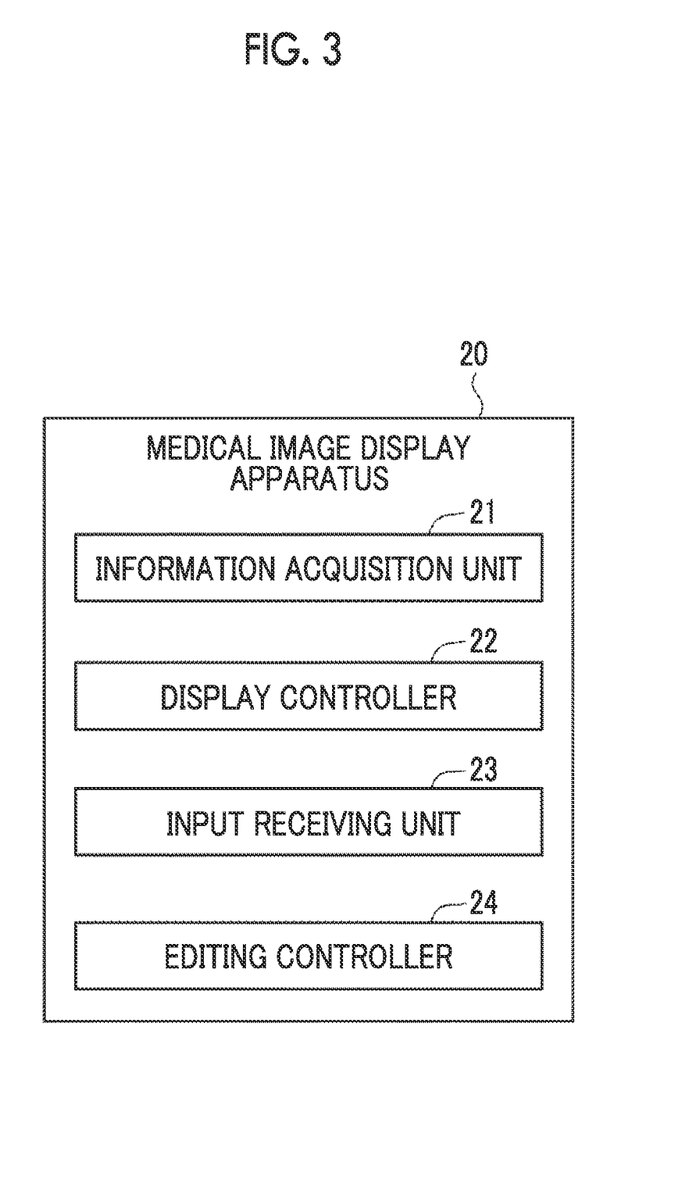
FIG. 3 is a functional configuration diagram of the medical image display apparatus according to the present embodiment.

Next, a functional configuration of the medical image display apparatus according to the present embodiment will be described. FIG. 3 is a diagram showing a functional configuration of the medical image display apparatus according to the present embodiment. As shown in FIG. 3, the medical image display apparatus 20 comprises an information acquisition unit 21, a display controller 22, an input receiving unit 23, and an editing controller 24. Then, in a case where the CPU 11 executes the medical image display program 12, the CPU 11 functions as the information acquisition unit 21, the display controller 22, the input receiving unit 23, and the editing controller 24.

The information acquisition unit 21 acquires a medical image G0 to be processed for creating an interpretation report from the image server 5 according to an instruction from the input device 15 by the radiologist who is an operator. In addition, according to the instruction from the input device 15, the analysis server 9 is instructed to analyze the medical image G0 to be processed, and the analysis result from the analysis server 9 is acquired.

The display controller 22 controls various displays including the display of the medical image G0 and the display of annotations representing each of the interpretation result and the analysis result to be described later.

The input receiving unit 23 receives the input of the interpretation result from the input device 15 by the radiologist, and outputs the input information to the display controller 22.

As will be described later, the editing controller 24 prohibits editing of the primary interpretation result input by the radiologist by the primary interpretation before displaying the annotation representing the analysis result after the annotation representing the analysis result is displayed. In addition, in a case where the annotation representing the analysis result is displayed, there is given a notification indicating that the editing of the primary interpretation result is prohibited. Further, the editing controller 24 saves the annotation representing the primary interpretation result and the annotation representing the secondary interpretation result input by the radiologist by the secondary interpretation after the annotation representing the analysis result is displayed in association with the medical image G0.

Figure 4:
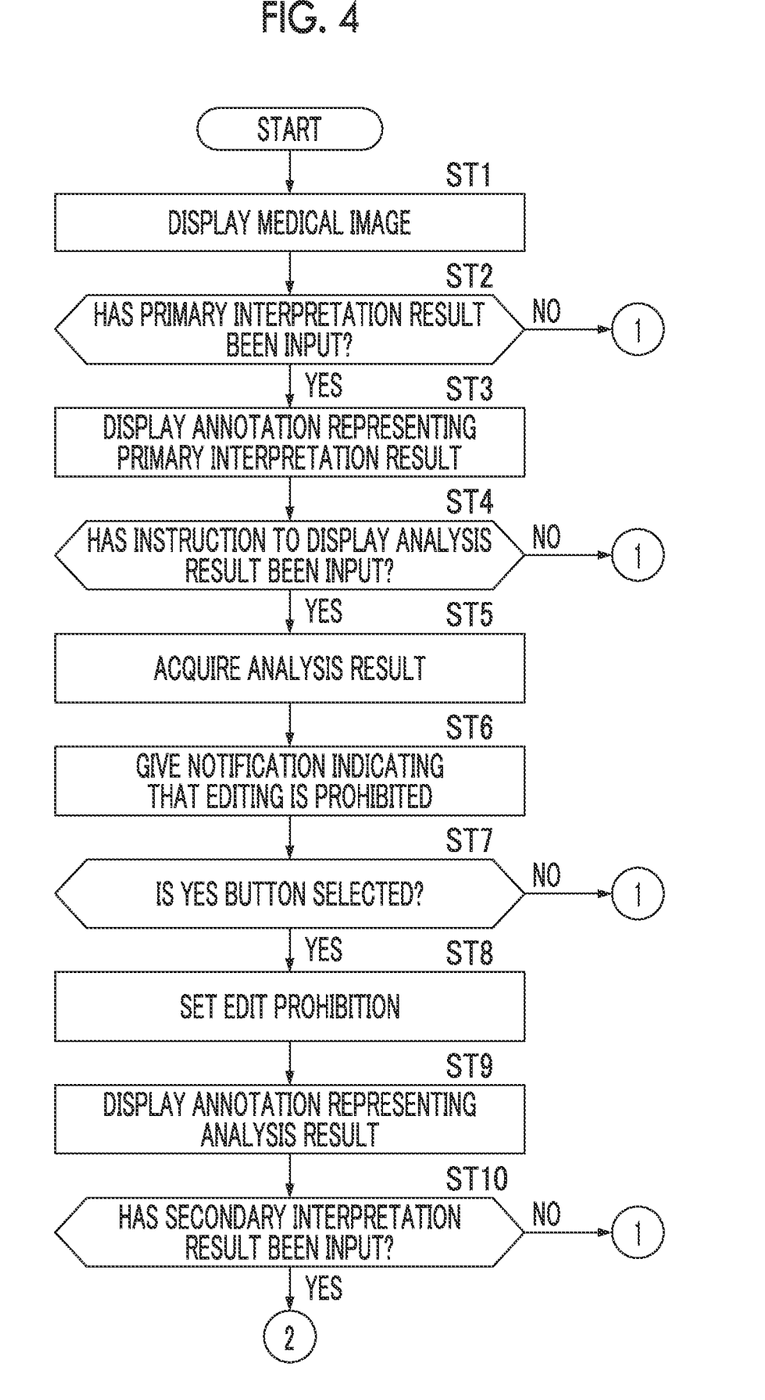
FIG. 4 is a flowchart showing a process performed in the present embodiment.
Figure 5:
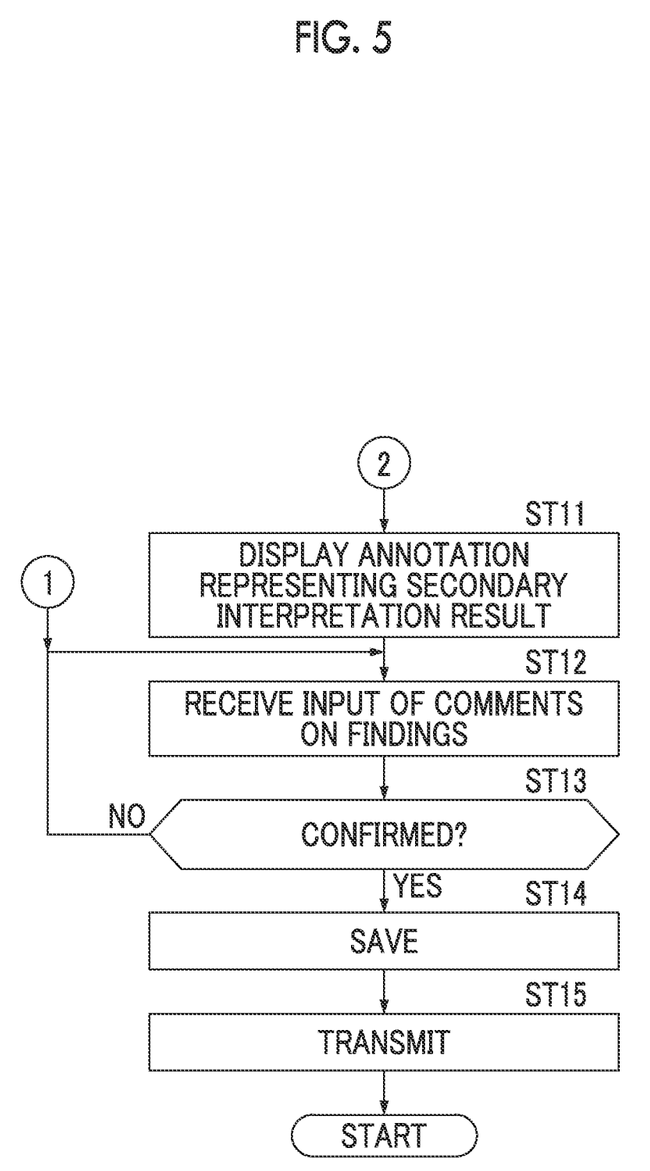
FIG. 5 is a flowchart showing a process performed in the present embodiment.

Hereinafter, a process performed in the present embodiment will be described in detail. FIGS. 4 and 5 are flowcharts showing a process performed in the present embodiment. Note that, it is assumed that the acquisition of the medical image G0 to be diagnosed and the instruction for analysis to the analysis server 9 have been completed. The process is started in a case where an instruction to create an interpretation report is given, and the display controller 22 displays the medical image G0 on the display 14 (Step ST1). Thereby, the radiologist performs the primary interpretation of the displayed medical image G0.

Figure 6:
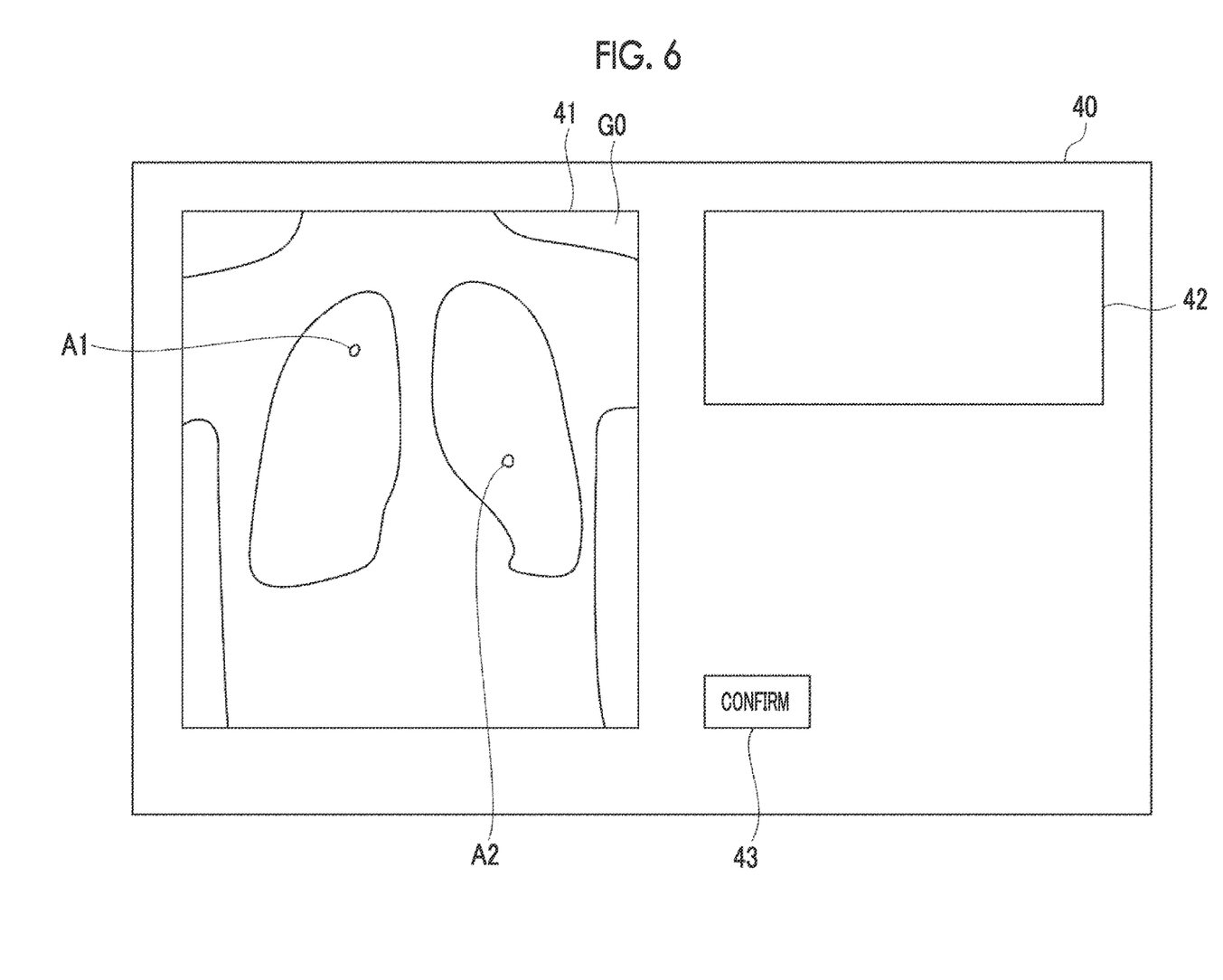
FIG. 6 is a diagram showing a display screen for primary interpretation.

FIG. 6 is a diagram showing a display screen for primary interpretation. As shown in FIG. 6, an image display region 41 and a sentence display region 42 are displayed on a display screen 40. Further, a confirmation button 43 for confirming the input content is also displayed. The medical image G0 is displayed in the image display region 41. As shown in FIG. 6, the medical image G0 is a radiation image of a chest of a human body. The medical image G0 includes two abnormal shadows A1 and A2. Further, in the sentence display region 42, comments on findings input by a radiologist are displayed.

Next, the input receiving unit 23 determines whether or not the primary interpretation result of the medical image G0 has been input by the radiologist (Step ST2), and in a case where Step ST2 is affirmative, the display controller 22 displays an annotation representing the primary interpretation result on the medical image G0 (Step ST3). In a case where Step ST2 is negative, the process proceeds to Step ST12.

Figure 7:
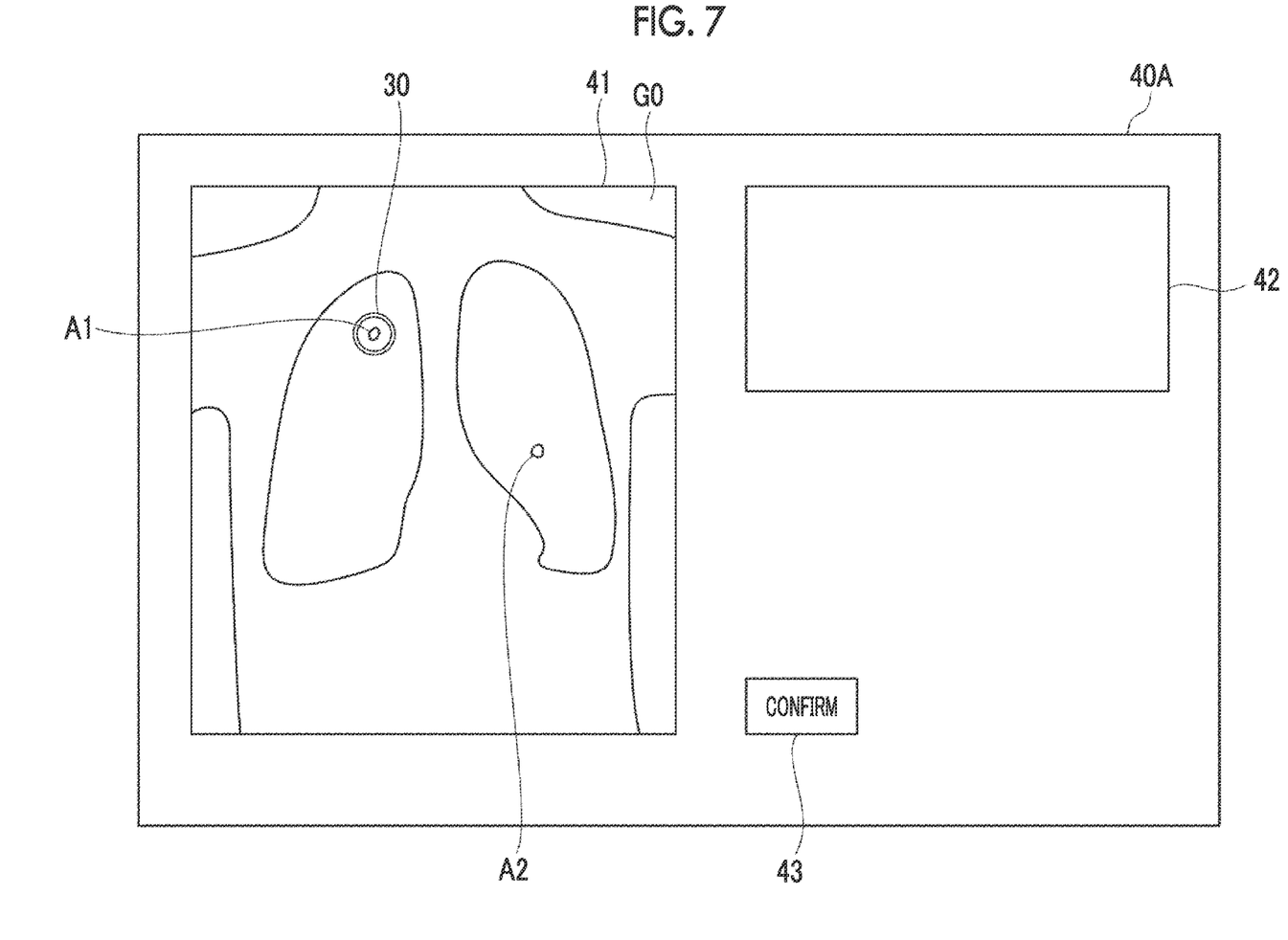
FIG. 7 is a diagram showing a display screen in which an annotation representing a primary interpretation result is displayed.

FIG. 7 is a diagram showing a display screen in which an annotation representing a primary interpretation result is displayed. As shown in FIG. 7, on the medical image G0 on a display screen 40A, a circular mark 30 is given to the abnormal shadow A1 specified by the radiologist by interpreting the medical image G0 as an annotation representing the primary interpretation result. Although only one mark 30 is displayed in FIG. 7, in a case where a plurality of abnormal shadows are found as a result of interpretation, a mark is given to each of them. The mark is not limited to a circle, but may have a polygonal shape, or may have any shape such as an arrow. Further, the annotation representing the primary interpretation result is not limited to the mark, and may be text in which the content of the doctor's interpretation result is described. In the case of text, the display region of the text is displayed as an annotation adjacent to the abnormal shadow. Further, here, for the sake of description, it is assumed that the abnormal shadow A2 is not specified by the primary interpretation.

Next, the input receiving unit 23 determines whether or not the instruction to display the analysis result has been input (Step ST4), and in a case where Step ST4 is affirmative, the information acquisition unit 21 acquires the analysis result of the medical image G0 (Step ST5). The analysis result may be acquired while the processes of Steps ST1 to ST4 are being performed, or may be acquired before the process of Step ST1. On the other hand, in a case where Step ST4 is negative, the process proceeds to Step ST12.

Figure 8:
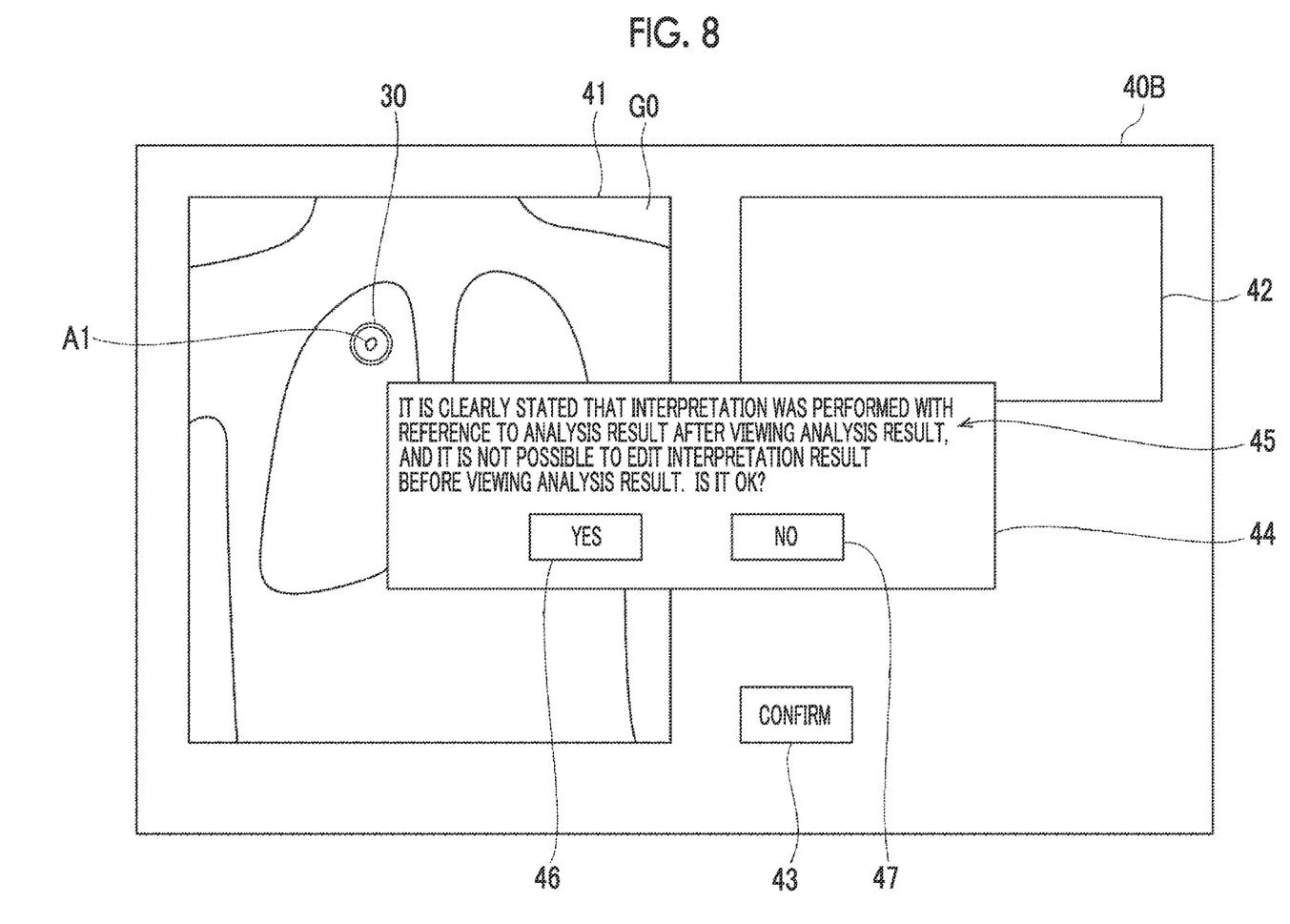
FIG. 8 is a diagram showing a display screen in which an edit prohibition notification is displayed.

Subsequently, the editing controller 24 gives a notification indicating that editing of the primary interpretation result input by the radiologist is prohibited (Step ST6). FIG. 8 is a diagram showing a display screen in which an edit prohibition notification is displayed. As shown in FIG. 8, an edit prohibition notification 44 is displayed on to display screen 40B. In the edit prohibition notification 44, text 45 "It is clearly stated that the interpretation was performed with reference to the analysis result after viewing the analysis result, and it is not possible to edit the interpretation result before viewing the analysis result. Is it OK?", a YES button 46, and a NO button 47 are displayed. In a case where the NO button 47 is selected (Step ST7; NO), the process proceeds to Step ST12, which will be described later.

In a case where the YES button 46 is selected (Step ST7; YES), the editing controller 24 sets the editing of the primary interpretation result to be prohibited (Step ST8). Specifically, an edit prohibition flag is set for information indicating the primary interpretation result (information indicating the position of the abnormal shadow and the type of the mark, and the like) so that the mark 30 which is an annotation representing the primary interpretation result cannot be deleted from the medical image G0, the type of the mark 30 cannot be changed, the position of the mark 30 cannot be changed, and the like. Then, based on the analysis result acquired by the display controller 22, an annotation representing the analysis result is displayed on the medical image G0 (Step ST9). At this time, the acquired analysis result information may be displayed as an annotation as it is, or the acquired analysis result may be processed and the information indicating the analysis result may be displayed as an annotation.

Figure 9:
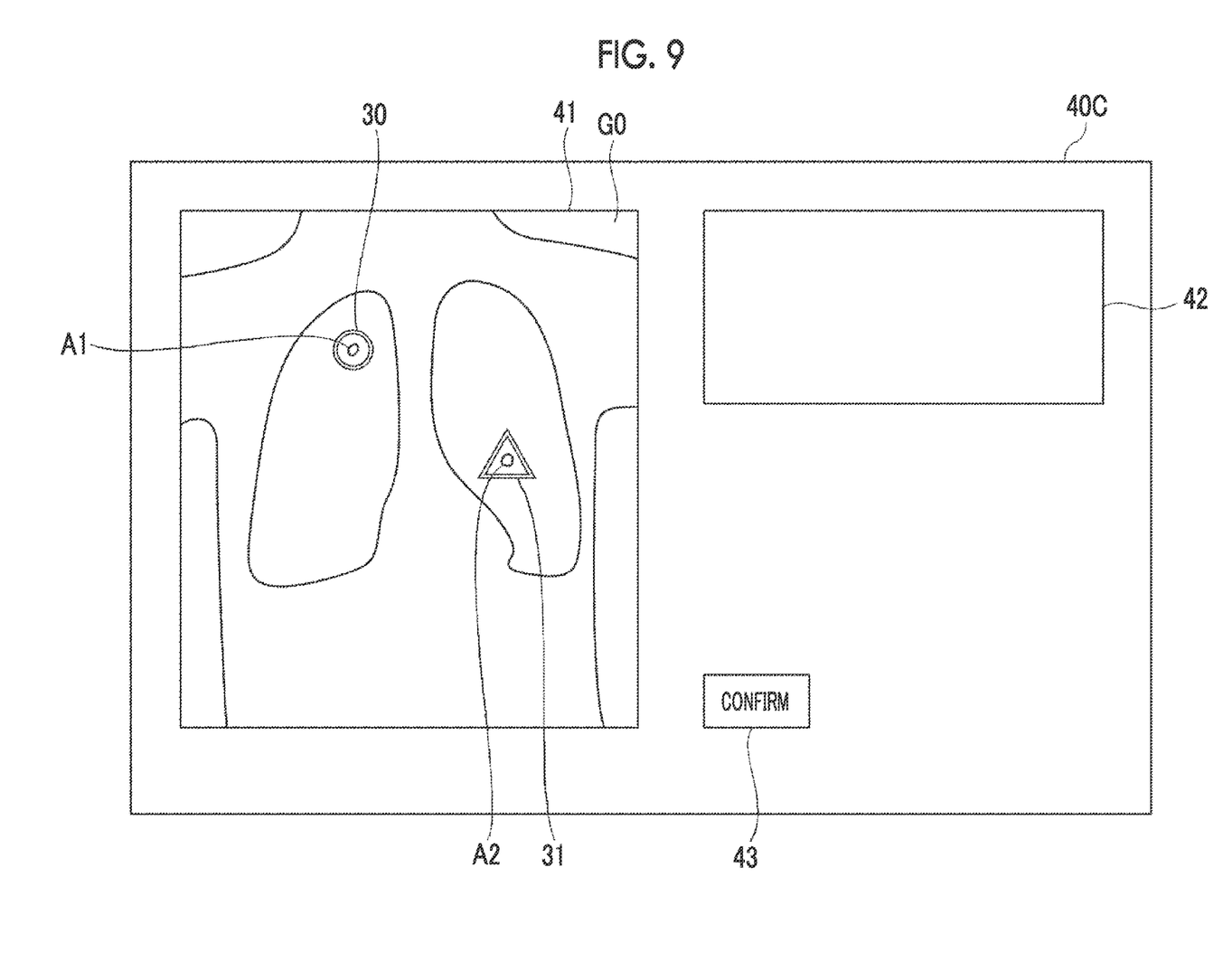
FIG. 9 is a diagram showing a display screen on which an annotation representing an analysis result is displayed.

FIG. 9 is a diagram showing a display screen on which an annotation representing an analysis result is displayed. As shown in FIG. 9, on the medical image G0 displayed on a display screen 40C, in addition to the circular mark 30 which is an annotation representing the primary interpretation result, a triangular mark 31 which is an annotation representing the analysis result is displayed.

Here, since the annotation representing the primary interpretation result is the circular mark 30 and the annotation representing the analysis result is the triangular mark 31, the annotation representing the primary interpretation result and the annotation representing the analysis result are displayed in a distinguishable manner. The mark 30 and the mark 31 may have different colors in addition to or instead of having different shapes, or may have different line types. After this, the radiologist refers to the analysis result and performs further interpretation of the medical image G0, that is, secondary interpretation.

As an annotation representing the analysis result, text indicating the property included in the analysis result may be displayed. In this case, a text box is associated with the abnormal shadow detected by the analysis result, and the property is described in the text box.

Next, the input receiving unit 23 determines whether or not the secondary interpretation result of the medical image G0 has been input by the radiologist with reference to the analysis result (Step ST10), and in a case where Step ST10 is affirmative, the display controller 22 displays an annotation representing the secondary interpretation result on the medical image G0 (Step ST11). In a case where Step ST10 is negative, the process proceeds to Step ST12.

Figure 10:
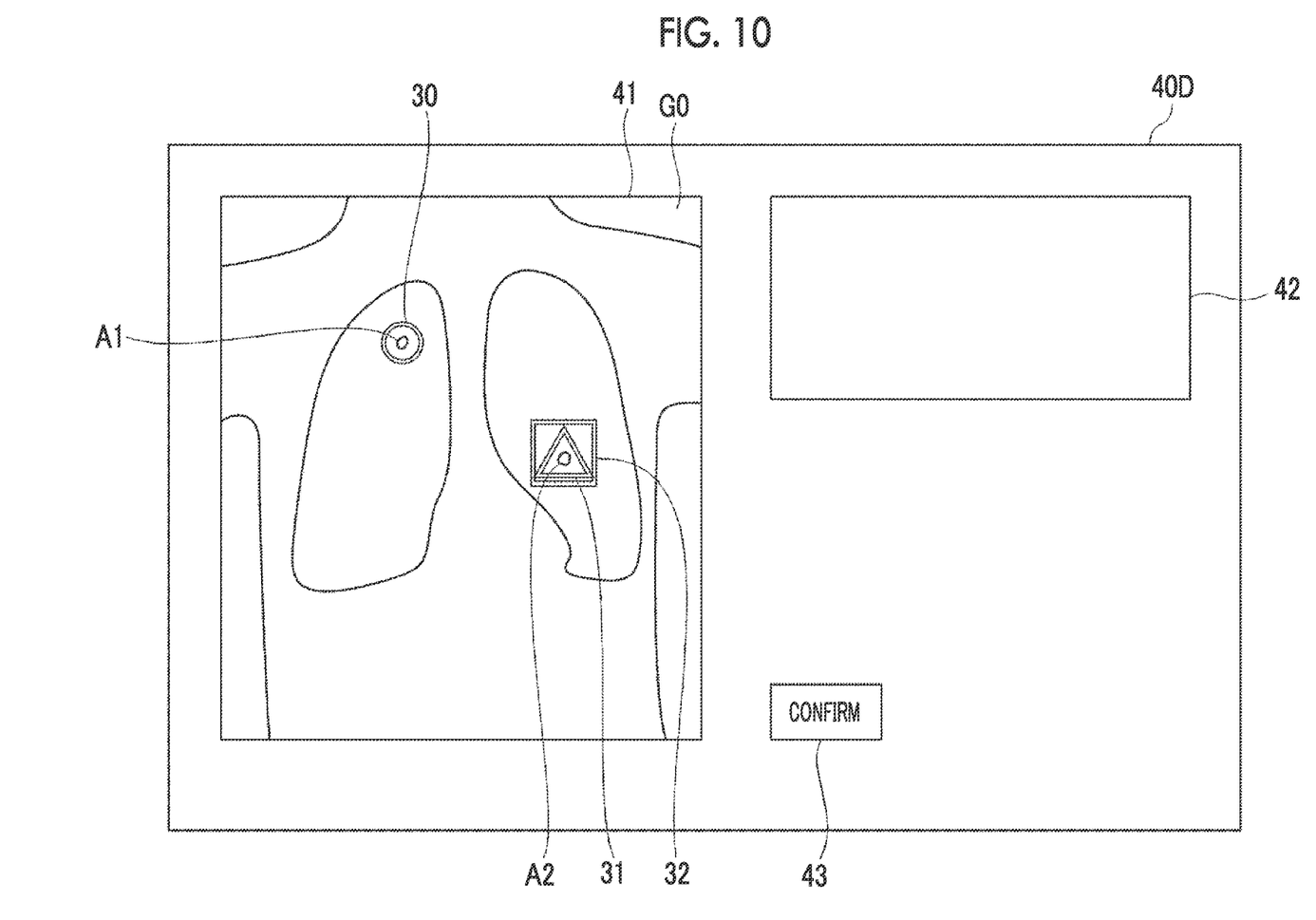
FIG. 10 is a diagram showing a display screen in which an annotation representing a secondary interpretation result is displayed.

FIG. 10 is a diagram showing a display screen in which an annotation representing a secondary interpretation result is displayed. As shown in FIG. 10, on the medical image G0 of a display screen 40D, in addition to the circular mark 30 which is an annotation representing the primary interpretation result and the triangular mark 31 which is an annotation representing the analysis result, a rectangular mark 32 which is an annotation representing the secondary interpretation result is displayed. Since the rectangular mark 32 is given to the abnormal shadow A2 specified by the analysis result, the triangular mark 31 and the rectangular mark 32 are displayed to overlap each other.

Here, since the annotation representing the primary interpretation result is the circular mark 30 and the annotation representing the secondary interpretation result is the rectangular mark 32, the annotation representing the primary interpretation result and the annotation representing the secondary interpretation result are displayed in a distinguishable manner. The mark 30 and the mark 32 may have different colors in addition to or instead of having different shapes, or may have different line types.

Subsequently, the editing controller 24 receives the input of the comments on findings by the radiologist to the sentence display region 42 (Step ST12). Then, the editing controller 24 determines whether or not the confirmation button 43 has been selected (Step ST13), and returns to Step ST12 in a case where Step ST13 is negative. In a case where Step ST13 is affirmative, the editing controller 24 saves the annotation representing the primary interpretation result and the annotation representing the secondary interpretation result in the medical image G0 in the storage 13 in association with the medical image G0 (Step ST14). In a case where the process of Step ST2 is negative, the annotation representing the interpretation result is not associated with the medical image G0. In a case where the processes of Steps ST4, ST7, and ST10 are negative, only the annotation representing the primary interpretation result is saved in association with the medical image G0.

Further, the editing controller 24 generates an interpretation report in which the comments on findings are described and transmits it to the report server 7, further transmits the medical image G0 saved in the storage 13 to the image server 5 (Step ST15), and ends the process.

Here, saving the annotation representing the primary interpretation result and the annotation representing the secondary interpretation result in association with the medical image G0 means that the annotation representing the primary interpretation result and the annotation representing the secondary interpretation result are saved to be integrally inseparable from the medical image G0. Specifically, a mode such as superimposing on the medical image G0 or writing in tag information of the medical image G0 can be employed. Thereby, when the medical image G0 is displayed later, by displaying the medical image G0 together with the annotation saved in association with the medical image G0, the annotation representing the primary interpretation result and the annotation representing the secondary interpretation result can be displayed in the same manner as the display screen 40C shown in FIG. 9 and the display screen 40D shown in FIG. 10.

In this way, in the present embodiment, the annotation representing the primary interpretation result before displaying the analysis result and the annotation representing the secondary interpretation result after displaying the annotation representing the analysis result are displayed in a distinguishable manner. Therefore, in the displayed medical image, it is possible to ascertain how the analysis result of the medical image via CAD affected the interpretation result of the doctor.

Further, by prohibiting the editing of the primary interpretation result after displaying the annotation representing the analysis result, it is possible to prevent the primary interpretation result from being modified by the radiologist before displaying the annotation representing the analysis result. Therefore, it is possible to more accurately ascertain how the analysis result of the medical image via CAD affected the interpretation result of the doctor.

In addition, by giving a notification indicating that the editing of the primary interpretation result is prohibited before the annotation representing the analysis result is displayed, the radiologist can know in advance that the editing of the primary interpretation result is prohibited. Therefore, it is possible to be more careful in displaying the analysis result, and as a result, it is possible to encourage the radiologist to perform the interpretation before displaying the analysis result more carefully.

Further, by saving the annotation representing the primary interpretation result and the annotation representing the secondary interpretation result in association with the medical image G0, in a case where the medical image G0 is displayed later, it is possible to ascertain how the analysis result of the medical image via CAD affected the interpretation result of the doctor.

Figure 11:
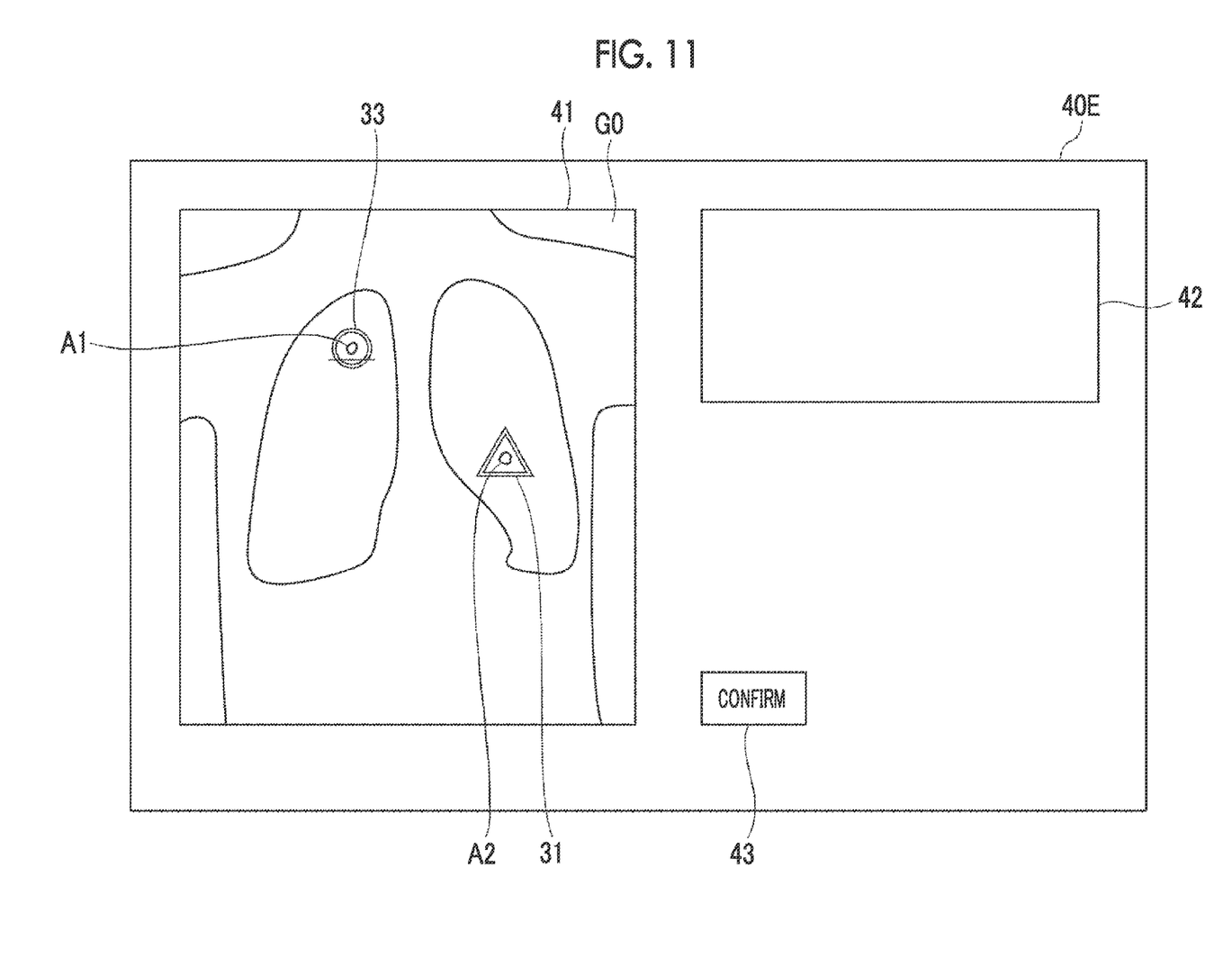
FIG. 11 is a diagram showing another display screen of an analysis result.

In the above embodiment, an annotation representing the primary interpretation result may be displayed on the display screen of the analysis result such that the prohibition of editing of the primary interpretation result is visually recognized. FIG. 11 is a diagram showing another display screen of an analysis result. In the medical image G0 displayed on a display screen 40E as shown in FIG. 11, a mark 33 representing an annotation representing the primary interpretation result is given a line extending in the lateral direction below the circular mark. Instead of the mark 33, the color of the mark 30 shown in FIG. 9 may be changed or the line may be thinned to make the prohibition of editing visually recognizable. Further, by displaying the text of the prohibition of editing as an annotation, it may be possible to visually recognize that the editing is prohibited.

Further, in the above embodiment, the analysis server 9 analyzes the medical image G0, but the present disclosure is not limited thereto. The interpretation WS 3 may analyze the medical image G0. In this case, in the interpretation WS 3, similarly to the analysis server 9, it may be performed by using a learning model in which machine learning is performed to detect abnormal shadows from the medical image.

Further, in the above embodiment, the annotations representing the primary interpretation result, the analysis result, and the secondary interpretation result are displayed in a distinguishable manner by different marks, but the present disclosure is not limited thereto. The annotations representing the primary interpretation result, the analysis result, and the secondary interpretation result may be displayed in a distinguishable manner by displaying text indicating the primary interpretation result as the annotation representing the primary interpretation result, and displaying text indicating the secondary interpretation result as the annotation representing the secondary interpretation result.

Further, in the above embodiment, the annotation representing the primary interpretation result and the annotation representing the analysis result are displayed in a distinguishable manner, but the present disclosure is not limited thereto. In the present embodiment, the annotation representing the primary interpretation result and the annotation representing the secondary interpretation result may be displayed in a distinguishable manner.

Further, in each of the above embodiments, the technique of the present disclosure is applied in the case of creating an interpretation report using a medical image with lung or liver as the diagnosis target, but the diagnosis target is not limited to lung or liver. In addition to the lung, any part of a human body such as a heart, brain, kidneys, and limbs can be diagnosed.

Further, in each of the above embodiments, for example, as hardware structures of processing units that execute various kinds of processing, such as the information acquisition unit 21, the display controller 22, the input receiving unit 23, and the editing controller 24, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. A medical image display apparatus comprising:
at least one processor, wherein the at least one processor is configured to:
display a medical image;
receive an input of an interpretation result of the medical image as a primary interpretation result;
acquire an analysis result for the medical image obtained by analyzing the medical image by an analysis computer with which the image display apparatus communicates;
prohibit editing of the primary interpretation result subsequent to an annotation representing the analysis result being displayed;
after prohibiting editing, display the annotation representing the analysis result;

after displaying the annotation representing the analysis result, receive an input of an interpretation result of the medical image as a secondary interpretation result;

display an annotation representing the secondary interpretation result in a distinguishable manner from the annotation representing the primary interpretation result; and generate an interpretation report and transmit the interpretation report to a report server.

2. The medical image display apparatus according to claim 1, wherein the at least one processor is configured to display the annotation representing the primary interpretation result and the annotation representing the secondary interpretation result in a distinguishable manner by displaying the annotation representing the primary interpretation result and the annotation representing the secondary interpretation result by means of at least one of marks having different colors or marks having different shapes.

3. The medical image display apparatus according to claim 1, wherein the at least one processor is configured to display the annotation representing the primary interpretation result and the annotation representing the secondary interpretation result in a distinguishable manner by displaying text indicating the primary interpretation result as the annotation representing the primary interpretation result, and displaying text indicating the secondary interpretation result as the annotation representing the secondary interpretation result.

4. The medical image display apparatus according to claim 1, wherein the at least one processor is configured to display the annotation representing the primary interpretation result and the annotation representing the analysis result in a distinguishable manner.

5. The medical image display apparatus according to claim 1, wherein the at least one processor is configured to give a notification indicating that editing of the primary interpretation result is prohibited before displaying the annotation representing the analysis result.

6. The medical image display apparatus according to claim 1, wherein the at least one processor is configured to display the annotation representing the primary interpretation result such that prohibition of the editing is visually recognized.

7. The medical image display apparatus according to claim 1, wherein the at least one processor is configured to save the annotation representing the primary interpretation result and the annotation representing the secondary interpretation result in association with the medical image.

8. A medical image display method comprising:
displaying, by a processor, a medical image at an image display apparatus;

receiving, by the processor, an input of an interpretation result of the medical image as a primary interpretation result;

acquiring, by the processor, an analysis result for the medical image obtained by analyzing the medical image by an analysis computer with which the image display apparatus communicates;

prohibiting, by the processor, editing of the primary interpretation result subsequent to an annotation representing the analysis result being displayed;

after prohibiting editing, displaying, by the processor, the annotation representing the analysis result at the image display apparatus;

after displaying the annotation representing the analysis result, receiving, by the processor, an input of an interpretation result of the medical image as a secondary interpretation result;

displaying, by the processor, an annotation representing the secondary interpretation result at the image display apparatus, in a distinguishable manner from the annotation representing the primary interpretation result; and generating, by the processor, an interpretation report and transmitting the interpretation report to a report server.

9. A non-transitory computer-readable storage medium that stores a medical image display program causing a computer to execute a procedure comprising:
displaying a medical image at an image display apparatus;

receiving an input of an interpretation result of the medical image as a primary interpretation result;

acquiring an analysis result for the medical image obtained by analyzing the medical image by an analysis computer with which the image display apparatus communicates;

prohibit editing of the primary interpretation result subsequent to an annotation representing the analysis result being displayed;

after prohibiting editing, displaying the annotation representing the analysis result;

after displaying the annotation representing the analysis result, receiving an input of an interpretation result of the medical image as a secondary interpretation result;

displaying an annotation representing the secondary interpretation result at the image display apparatus in a distinguishable manner from the annotation representing the primary interpretation result; and generating an interpretation report and transmitting the interpretation report to a report server.

* * * * *